(12) United States Patent
Noguchi et al.

(10) Patent No.: US 8,122,804 B2
(45) Date of Patent: Feb. 28, 2012

(54) SLICING GUIDE DEVICE FOR PREPARING TEXTURE SLICES, TEXTURE SLICES PREPARING DEVICE, AND METHOD FOR PREPARING TEXTURE SLICES

(75) Inventors: Masanori Noguchi, Kurume (JP); Shigetaka Suekane, Kurume (JP); Kei Matsuoka, Kurume (JP)

(73) Assignee: Kurume University, Fukuoka (JP)

( * ) Notice: Subject to any disclaimer, the term of this patent is extended or adjusted under 35 U.S.C. 154(b) by 329 days.

(21) Appl. No.: 12/513,238

(22) PCT Filed: Oct. 31, 2007

(86) PCT No.: PCT/JP2007/071202
§ 371 (c)(1),
(2), (4) Date: May 1, 2009

(87) PCT Pub. No.: WO2008/053916
PCT Pub. Date: May 8, 2008

(65) Prior Publication Data
US 2010/0050838 A1  Mar. 4, 2010

(30) Foreign Application Priority Data
Nov. 1, 2006 (JP) ................................. 2006-297869

(51) Int. Cl.
*B26D 5/08* (2006.01)
*B26D 3/00* (2006.01)
(52) U.S. Cl. .............. 83/607; 83/765; 83/915.5; 83/870
(58) Field of Classification Search .................... 83/607, 83/167, 765, 761, 609, 919, 915.5, 606, 932, 83/870; 269/287
See application file for complete search history.

(56) References Cited

U.S. PATENT DOCUMENTS
194,417 A * 8/1877 Davis .............................. 83/762
(Continued)

FOREIGN PATENT DOCUMENTS
EP  1149275 A2  6/2000
(Continued)

OTHER PUBLICATIONS
"Brain Slicer for a Rat or Mouse", website http://www.muromachi.com/products/Physio/aster.html, last updated Mar. 17, 2004.

*Primary Examiner* — Boyer D Ashley
*Assistant Examiner* — Omar Flores Sanchez
(74) *Attorney, Agent, or Firm* — Day Pitney LLP

(57) ABSTRACT

Provided are a cutting guide device for preparing a texture section, which can prepare a texture section manually with a cutting tool such as a pathological knife, in a uniform thickness and in a regular section with neither experience nor skill, a texture section preparing device, and a method for preparing a texture section. The texture section preparing cutting guide device includes a placing base for placing a texture mass directly or indirectly thereon, and a cutting guide cover for preventing the texture mass placed directly or indirectly on the placing base from moving, by holding the texture mass downward. In at least such a portion of the cutting guide cover as to hold the texture mass, there are formed a plurality of slits, into which a knife to be used to cut the texture mass can be inserted. The slits have their intervals set to the thickness of a desired texture section.

20 Claims, 6 Drawing Sheets

U.S. PATENT DOCUMENTS

| | | | | |
|---|---|---|---|---|
| 703,588 A | * | 7/1902 | Ivey | 83/145 |
| 1,468,546 A | * | 9/1923 | Russo | 83/466.1 |
| 1,685,245 A | * | 9/1928 | Russo | 83/578 |
| 1,703,154 A | * | 2/1929 | Lanzkron | 83/762 |
| 1,764,235 A | * | 6/1930 | Wilmking | 83/762 |
| 4,383,365 A | * | 5/1983 | Metzigian | 30/114 |
| 4,589,206 A | * | 5/1986 | Marcoux | 30/114 |
| 5,386,755 A | * | 2/1995 | Schneider et al. | 83/762 |
| 5,499,578 A | * | 3/1996 | Payne | 99/537 |
| 6,148,704 A | * | 11/2000 | Lewis | 83/167 |
| 6,289,682 B1 | * | 9/2001 | Rada | 62/51.1 |
| 7,455,005 B2 | * | 11/2008 | Giessler | 83/605 |

FOREIGN PATENT DOCUMENTS

| | | |
|---|---|---|
| JP | 2-57854 B1 | 12/1990 |
| JP | 2002-533670 A | 10/2002 |
| JP | 2005-98702 A | 4/2005 |
| WO | WO-00/37918 A2 | 6/2000 |
| WO | WO-01/27586 A1 | 4/2001 |

* cited by examiner

SLICING GUIDE DEVICE FOR PREPARING TEXTURE SLICES, TEXTURE SLICES PREPARING DEVICE, AND METHOD FOR PREPARING TEXTURE SLICES

CROSS REFERENCES TO RELATED APPLICATION

This is a U.S. national phase application under U.S.C. §371 of International Patent Application No. PCT/JP2007/071202, filed Oct. 31, 2007 which claims priority to Japanese Application No. 2006-297869, filed Nov. 1, 2006. The International Application was published on May 8, 2008 as International Publication No. WO/2008/053916 under PCT Article 21(2) the contents of which are incorporated herein in its entirety.

TECHNICAL FIELD

The present invention relates to a cutting guide device for preparing texture slices, texture slices preparing device, and a method for preparing a texture slices.

More specifically, the present invention relates to a cutting guide device for preparing a texture slices, which enables an operator to manually cut a texture slices with a cutting tool such as a pathological knife, in the same thickness, and having regular and smooth surfaces each with neither experience not skill, a texture slice preparing device, and a method for preparing texture slices.

BACKGROUND OF THE INVENTION

When performing detailed pathological examinations, preparation of a holoblastic specimen for organic texture may be required. More specifically, a detailed pathological examination is performed by slicing the texture in its entirety to prepare slice sections, each of the specimen is adhered to a glass slide to be examined with a microscope.

Usually, a texture slice is prepared manually with a slicing knife such as a special pathological knife for slicing a larger texture mass of parenchymal organs such as prostate gland, lacteal gland, lung, liver, heart, and others. For example, to examine a holoblastic specimen of a prostate tissue after a surgery is performed for a prostate cancer, sliced samples should be prepared in a uniform thickness of approximately 3 mm, each having smooth surfaces each.

However, texture mass is generally highly deformable due to its softness, flexibility and elasticity. Further, as described above, because the texture mass should be sliced in a uniform thickness manually with a pathological knife, the operations would be a possibility to injure his finger tips with the knife. Therefore, it is difficult to prepare texture slices in a uniform thickness and having smooth surfaces without experience and skill. Further, even for those with experience and skill needs significant amount of time.

For example, Muromachi Kikai Co. (at http://www.muromachi.com/products/Physio/aster.html) ("Muromachi") presents a block called "brain slicer" for preparing slices of brain of a mouse or a rat. This block for preparing slices of brain is made by hollowing out an acrylic resin block in a shape of a brain for putting a sample of brain of a mouse or a rat. The block comprises slits formed at equal space intervals (1 mm, 2 mm or 3 mm), into which razors are inserted to obtain fresh brain slices.

However, if the block for preparing brain slices presented in Muromachi were resized and used for block tissues of human body, the following problems might occur.

As described above, because a texture mass of a parenchymal organ is soft with high flexibility and elasticity, the texture mass cannot be fixed properly only by inserting the texture mass into a hollow of the block on which brain slices are prepared. That is, even when efforts are made to slice the mass in a straight line, the texture mass tends to be moved to the side or deformed to cause irregular cross sections due to the weight of the pathological knife inserted from above.

Further, the block for preparing brain slices is made for slicing only brain samples of small animals, such as mice and rats. The brain sample of a small animal is much smaller than that of human's, and is less variable in size and shape for each individual. On the other hand, a texture mass of a human body varies considerably in size and shape depending on the organs or individual differences of the same organ. Therefore, it is extremely difficult to prepare in advance many blocks provided with various hollows that accommodate such different sized objects.

One of the purposes of the present invention is to prepare texture slices manually with a slicing tool such as a pathological knife, in uniform thicknesses and having smooth surfaces with neither experience nor skill for this operation.

Another purpose of the present invention is, in addition to the purpose described above, to allow an operator to slice even a texture mass of various sizes and thicknesses.

Further, another purpose of the present invention will be explained further hereinafter.

SUMMARY OF THE INVENTION

The means for achieving the purposes in the present invention will be described hereinafter.

Codes with parenthesis are used in drawings for easy understanding of the effects described hereinafter, however, the constituent elements are not limited to the codes provided in the drawings. The present invention pertains to a cutting guide device for slicing thinly a texture mass to obtain texture slices, having a placing base for placing a texture mass directly or indirectly thereon; and a cutting guide cover for preventing the texture mass placed directly or indirectly on the placing base from moving by holding the texture mass downward, wherein; a plurality of slits, into which a knife to be used for cutting the texture mass can be inserted, is formed at least in such a portion of the cutting guide cover which presses the texture mass downward; and the plurality of slits are provided with intervals therebetween which are set to the thickness of each desired texture slices.

The present invention pertains to a cutting guide device for slicing thinly a texture mass to obtain texture slices, having a placing base for placing a texture mass directly or indirectly thereon; a cutting guide cover for preventing the texture mass placed directly or indirectly on the placing base from moving by holding the texture mass downward, wherein; a contacting part with the texture mass formed so as to curve or protrude in an opposite direction to the pressing direction; a plurality of slits, into which a knife to be used for slicing the texture mass can be inserted, is formed at least in such a part of the cutting guide cover which presses the texture mass downward; and the plurality of slits are provided with intervals therebetween which are set to the thickness of desired texture slices.

The present invention pertains to a cutting guide device for slicing a texture mass to obtain a texture section, provided with a means for supporting the turnable cutting guide cover on a shaft so that the cutting guide cover can hold the texture mass downward and for adjusting the height of the portion supported on the shaft.

The present invention pertains to a cutting guide device for slicing a texture mass to obtain texture slices including a placing base for placing a texture mass directly or indirectly thereon; a cutting guide cover for preventing the texture mass placed directly or indirectly on the placing base from moving by holding the texture mass downward, in a manner in which an end potion side turns around fulcrum shafts provided on the base side portion; and a slippage preventing means for pressing the cutting guide cover to prevent the texture mass from slipping off; wherein, a contacting part is formed so as to be curved or protruded in an opposite direction to the pressing direction; a plurality of slits, into which a knife for cutting the texture mass can be inserted, is formed at the contacting portion; and the plurality of slits are provided with intervals therebetween which are set to the thickness of desired texture slices; the placing base has bearing portions which support and enable the fulcrum shafts of the cutting guide cover to turn on the shaft and to be removable and replaceable; the bearing portions have opening portions, or pores or insections, which guide fulcrum shafts to move in a vertical direction with respect to the fulcrum shafts for adjusting the height of the fulcrum shafts.

The present invention pertains to texture slices preparing device for preparing texture slices by slicing thinly a texture mass, including a cutting guide device as set forth in either of the above mentioned paragraphs; and an texture embedment preparing portion for preparing an embedded texture mass; wherein, the texture embedment preparing portion has a texture placing portion having a placing surface for the texture mass and a frame constituting element which is so combined with the texture placing portion to act together with the placing surface to comprise a housing portion for accommodating the texture mass and an embedding agent.

The invention pertains to texture slices preparing device for preparing texture slices by slicing a texture mass, having a cutting guide device set forth in either of above mentioned paragraphs; and an texture embedment preparing portion for preparing an embedded texture mass, wherein; the texture embedment preparing portion includes a texture placing portion having a placing surface for the texture mass, and a frame member which is so combined with the texture placing portion to act together with the placing surface, to comprise a housing portion for accommodating the texture mass and an embedding agent, and also to adjust the area of the housing portion.

The present invention pertains to texture slices preparing device for preparing texture slices by slicing a texture mass, including a cutting guide device as set forth in either of the paragraphs; and an texture embedment preparing portion for preparing an embedded texture mass, wherein; the texture embedment preparing portion comprises a texture placing portion that has a placing surface for the texture mass and a pair of frame member arranged face to face on the texture placing portion so as to act together with the placing surface to comprise a housing portion for accommodating the texture mass and an embedding agent and to adjust the area of the housing portion by changing the combination positions.

The present invention pertains to texture slices preparing device, wherein; a magnet is provided on either or both of a placing base of a cutting guide device and a texture placing portion of a texture embedment preparing portion for generating an attractive force between the placing base and texture placing portion, the attractive force of the magnet is in a degree that allows the texture placing portion to be movable or removable with respect to the placing base.

The present invention pertains to a method for preparing texture slices, comprising a method for preparing texture slices by slicing thinly a texture mass, wherein; at least one of the surface or a lower side of the texture mass embedded by an embedding agent is placed directly or indirectly on a placing base; the texture mass is pressed from above to be held between the placing base and the cutting guide cover by the cutting guide cover having a plurality of slits, of which intervals are set to the thickness of desired texture slices; and in a state, that the texture mass is held, a knife is inserted along the plurality of slits for cutting the texture mass with the embedding agent to prepare texture slices.

The present invention pertains to a method for preparing texture slices using a dental impression material as the embedding agent.

A texture mass to be cut can be, for example, human parenchymal organs, specifically, prostate gland, lacteal gland, lung, liver, heart, pancreas, spleen, brain, glandula thyreoidea, ovaria, and testis. However, these are typical examples and are not limited objects to be cut. Not to mention, texture mass of animals other than humans, for example, experimental animals, such as a mouse and a rat, can be used.

In the present specification and paragraphs in scope of claims, the word, knife, indicates knives overall and used in a broader concept. For example, knives, such as pathological knives, as well as razors and other blades are included.

Further, as previously described, the space intervals between the slits formed at the cutting guide cover are set to the thickness of a desired texture section. For example, when a texture section with 1~3 mm thickness is needed, the intervals between the slits can be set accordingly.

Further, as the dental impression material, alginate impression material and silicone rubber impression material can be used. Alginate impression material (also called alginic acid salt impression material) is used for making various molds of such as teeth and others in the dental field, because it becomes to hard gel by a chemical reaction between alginate salt, an active ingredient, and gelatinization reagents such as calcium sulfate, etc.

Operation of the cutting guide device for preparing a texture section related to the present invention will be described hereinafter. The cutting guide device includes a placing base and a cutting guide cover. The texture mass, at least one surface or a lower side being covered and embedded by an embedding agent, is placed directly or indirectly on the placing base. Embedding the texture mass with the embedding agent prevents the texture mass from becoming deformed and, further, off position.

After the texture mass placed on the placing base, the texture mass is pressed downward by the cutting guide cover. By this, the texture mass is held between the placing base and the cutting guide cover. Then, a knife is inserted along one of the plurality of slits formed at the cutting guide cover for slicing the texture mass with the embedding agent. After the cutting, the embedding agent is removed and the desired texture slices are obtained.

Because the texture mass of parenchymal organs and others is soft with high flexibility and elasticity, as previously described, by pressed downward with a cutting guide cover on which a plurality of slits is formed, a part of upper side of the texture mass is dug into each of the plurality of slits. By this, the texture mass is prevented from being deformed or moved, when it is under a load by a knife when cutting, accordingly, the texture section is prevented from forming irregular cross-section surfaces.

Furthermore, the width of the intervals of the plurality in the plurality of slits that are formed at the cutting guide cover is set according to the thickness of the desired texture section. Thus, when a knife is inserted along one of the plurality of slits for cutting the texture mass, the texture slices with uniform thickness can be prepared easily without experience and skill.

Further, as previously described, because the texture mass is prevented from moving by held between the placing base and the cutting guide cover, a texture mass in various thickness and shape can be used flexibly.

Further, a contacting portion curved or protruded in the opposite direction to the pressing direction is preferably provided, at least at a place where the texture mass is pressed with the cutting guide cover. Generally, a texture mass of thick parenchymal organs, for example, prostate gland, lacteal gland, lung, liver, heart, has a rounded outer shape. Thus, by making the contacting portion curved or protruded to fit the roundness, the tissue mass is entirely pressed by uniform suppression strength as far as possible to prevent from deformation of the texture mass. By this, irregularity of resulting texture cross-section is securely prevented.

In a device having a means which supports the turnable cutting guide cover on a shaft up and down for pressing the texture mass downward, and adjusts the height of the supported part of the cutting guide cover, the height can be adjusted to the thickness of the object to be cut, the texture mass. By this, a texture mass in various thickness can be used flexibly.

In this operation, the texture mass is preferably pressed under the condition in which the cutting guide cover is held on the level as far as possible by adjusting the height of the part which is supported on the shaft of the cutting guide cover. By this, for example, comparing to the condition in which the texture mass is pressed downward at an angle by the cutting guide cover, the downward force is prevented from being applied excessively only to a part of the texture mass and, accordingly, deformation of the texture mass is prevented. By this, irregularity of the obtained texture section can be more securely prevented.

When a slippage preventing means is provided, because the slippage preventing means prevents the pressing position of the cutting guide cover for the texture mass from slipping off, even if a hand or a knife contact the cutting guide cover during the cutting, the texture mass can be cut in a straight line.

Further, in a case in which the placing base is provided with bearing portions which support fulcrum shafts of the cutting guide cover, the fulcrum shafts are moved using opening portions, or pores or insections, formed at the bearing portions, so that the height of the fulcrum shafts of the cutting guide cover is adjusted.

Furthermore, the fulcrum shafts of the cutting guide cover are removable from the bearing portions, when removed from the placing base after use, the cutting guide cover can be washed. Thus, even when the placing base has a substantial weight, the cutting guide cover which contacts the texture mass can be washed easily.

Additionally, it is very convenient that the cutting guide cover can be replaced accordingly to those in different modes, which have different intervals of the plurality of slits or fit to the texture mass in different shapes.

The aforementioned cutting guide device which has texture slices and a texture embedment preparing portion operates as follows:

The texture embedment preparing portion includes a texture placing portion and a frame structuring part which act together to provide a housing portion.

Here, the housing portion is formed on the placing base of the cutting guide device by combining the texture placing portion and the frame structuring part, which are components of the texture embedment preparing portion for housing a texture mass and an embedding agent. Then, the texture mass and the embedding agent are put for embedment in the housing portion.

Next, the frame structuring part is removed from the texture placing portion leaving the embedded texture mass on the placing surface of the texture placing portion.

As previously described, the texture placing portion of the texture embedment preparing portion operates as a bottom part of an embedding container during the embedment and as a member on which the texture mass is placed when the texture mass is set on the cutting guide device. Therefore, when the texture embedment preparing portion relating to the present invention is in use, the texture mass can be set on the cutting guide device without touched by hand after embedded. Accordingly, when embedded properly, the texture mass is prevented from corruption or deformation caused by hand touching.

Further, contrary to a case in which the texture mass is placed directly on the cutting guide device, the texture placing portion can be washed thoroughly after use. Thus, even when the cutting guide device has a substantial weight, washing is easily performed.

When the texture embedment preparing portion includes a frame member which can adjust the area of the housing portion, the area of the housing portion is adjusted corresponding to the size of the texture mass, thereby using the appropriate amount of the embedding agent.

When the cutting guide device is provided with a magnet between the placing base and the texture placing portion of the texture embedment preparing portion, even if the placing base and the texture placing portion are made with slippery material, for example, a stainless-steel, the slipperiness is prevented by the attractive force of the magnet. Therefore, the texture mass which is held by the cutting guide cover is prevented from inconvenience such as slippage.

Further, when an opposite force to the attractive force of the magnet is applied to move the texture placing portion, the position of the texture mass corresponding to the cutting guide cover can be adjusted properly even after the texture mass is placed on the placing base. Accordingly, cutting operation can be performed easily at the most suitable position.

The present invention has the aforementioned structures, and the effect will be described hereinafter.

According to the cutting guide device for preparing texture slices, the device for preparing texture slices and the method for preparing the texture slices relating to the present invention, in a case in which the texture slices are prepared by a blade, such as a pathological knife, the texture slices can be prepared in uniform thickness and in regular slices having smooth surfaces, respectively with neither experience nor skill. Further, even the texture mass in various thickness can be used flexibly.

According to the cutting guide device for preparing texture section having a removable cutting guide cover, because the cutting guide cover can be removed from the main body of the cutting guide device, washing of the guide cover is performed easily. Further, it is very convenient that the cutting guide cover can be replaced accordingly to those in different modes, which have different intervals of the plurality of slits or fit to the texture mass in different shapes.

When a texture section preparing device is provided with the texture embedment preparing portion, the texture mass can be set on the cutting guide device without being touched by hand after being embedded. Accordingly, when embedded properly, the texture mass is prevented from corruption or deformation caused by hand contact. Further, contrary to the case in which the texture mass is placed directly on the cutting guide device, the texture placing portion can be washed thoroughly after use. Thus, even when the cutting guide device has a substantial weight, washing is easily performed.

In a case in which the texture embedment preparing portion which can adjust the area of the housing portion for housing the texture mass and embedding agent is provided, the appropriate amount of the embedding agent is used, therefore, it minimizes wasteful use of the embedding agent used.

When a cutting guide device includes a magnet settled between the placing base and the texture mass placing portion, the feature can prevent inconveniences, for example, in which the texture mass pressed by the cutting guide cover slips out of the place by the slippage of the texture placing portion. Further, even after the texture mass is placed on the texture placing portion, the position of the texture mass corresponding to the cutting guide cover can be adjusted properly to allow the cutting operation to be performed at the best position.

By using a dental impression agent as an embedding agent, a texture mass in various size and shape can be embedded properly, cutting operations can be performed by a blade such as a pathological knife and others, and texture slices can be obtained without irregular sections such as rough surface section or uneven thickness. Further, because alginate impression material or silicone rubber impression material become solidified from liquid state form or paste form, in a very short time, texture embedding operation is performed efficiently. Furthermore, alginate impression material is preferable, because alginate impression material can be removed with great ease from the obtained texture section after cut and prevents damage of a thin texture section.

DETAILED DESCRIPTION OF THE INVENTION

An embodiment of the present invention will be explained hereinafter, but the present invention is not limited to the embodiment.

The present invention will be explained based on the embodiment indicated in drawings.

FIG. 1 to FIG. 5 are explanatory views illustrating an embodiment of the texture section preparing device relating to the present invention.

Figure 1:
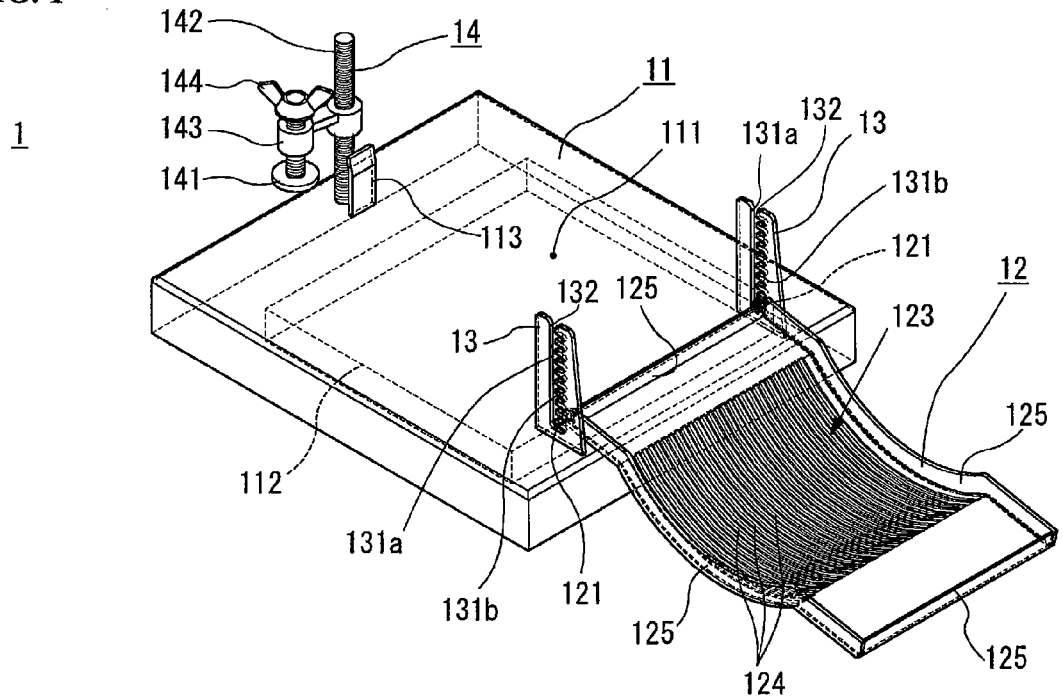
FIG. 1 is an explanatory oblique view of a cutting guide device comprising texture slices preparing device, illustrating a condition in which an openable and closable cutting guide cover is opened.

FIG. 1 is an explanatory oblique view of a cutting guide device comprising a texture section preparing device, illustrating a condition in which an openable and closable cutting guide cover is opened.

Figure 2:
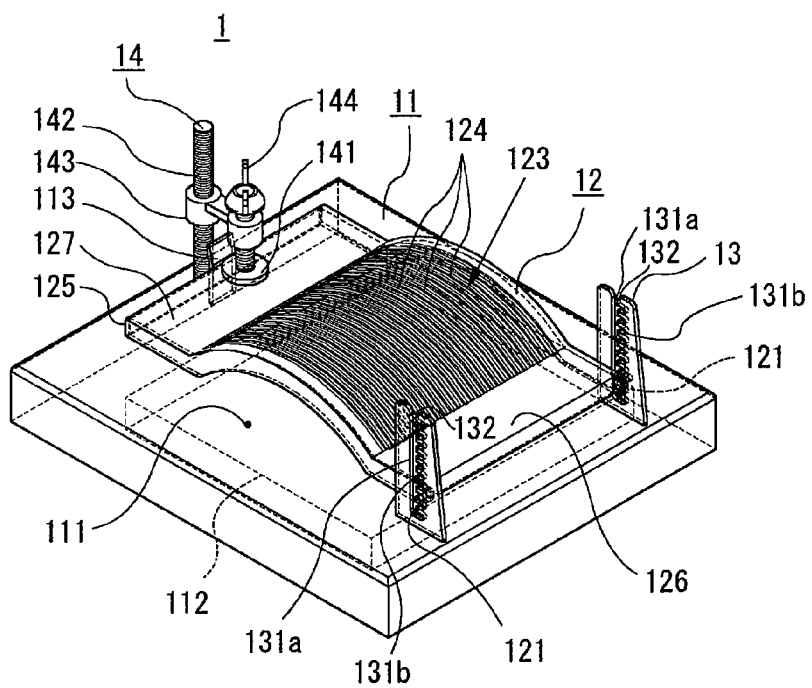
FIG. 2 is an explanatory oblique view of the cutting guide device shown in FIG. 1, illustrating a condition in which a cutting guide cover is closed.

FIG. 2 is an explanatory oblique view of the cutting guide device shown in FIG. 1, illustrating a condition in which a cutting guide cover is closed.

Figure 3:
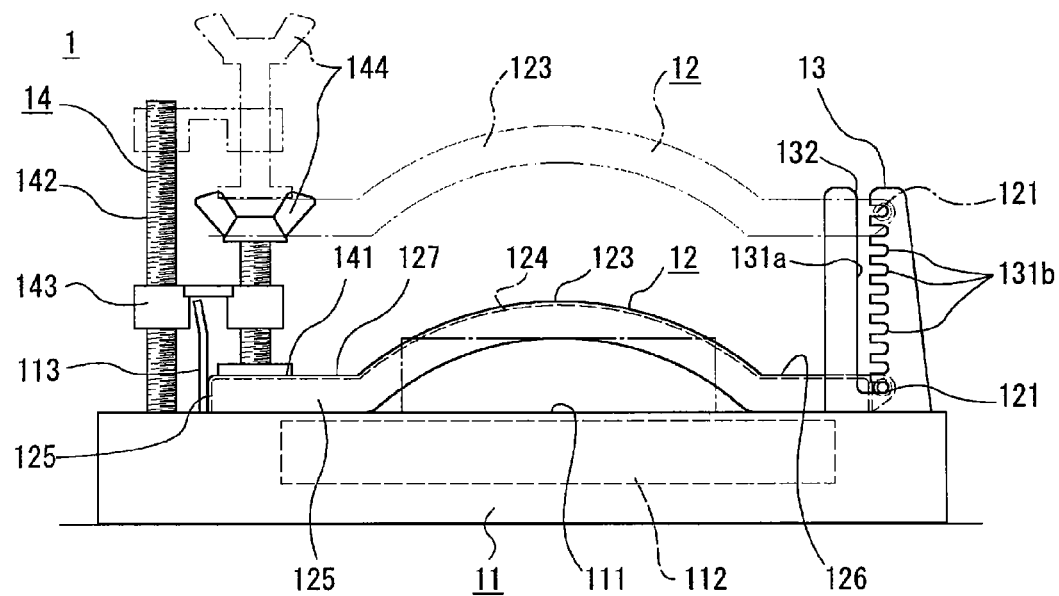
FIG. 3 is an explanatory side view of FIG. 2, illustrating, a condition in a imaginary line, a dashed-dotted line, in which a closed cutting guide cover is moved upward from a placing base.

FIG. 3 is an explanatory side view of FIG. 2, illustrating, a condition in an imaginary line, a dashed-dotted line, in which a closed cutting guide cover is moved upward from a placing base.

Figure 4:
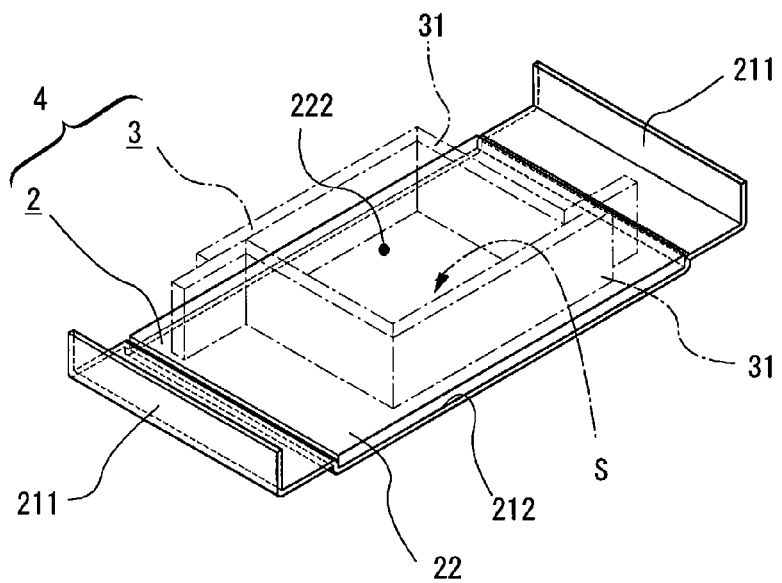
FIG. 4 is an explanatory oblique view of a texture embedment preparing portion placed on the cutting guide device shown in FIG. 1.
Figure 5:
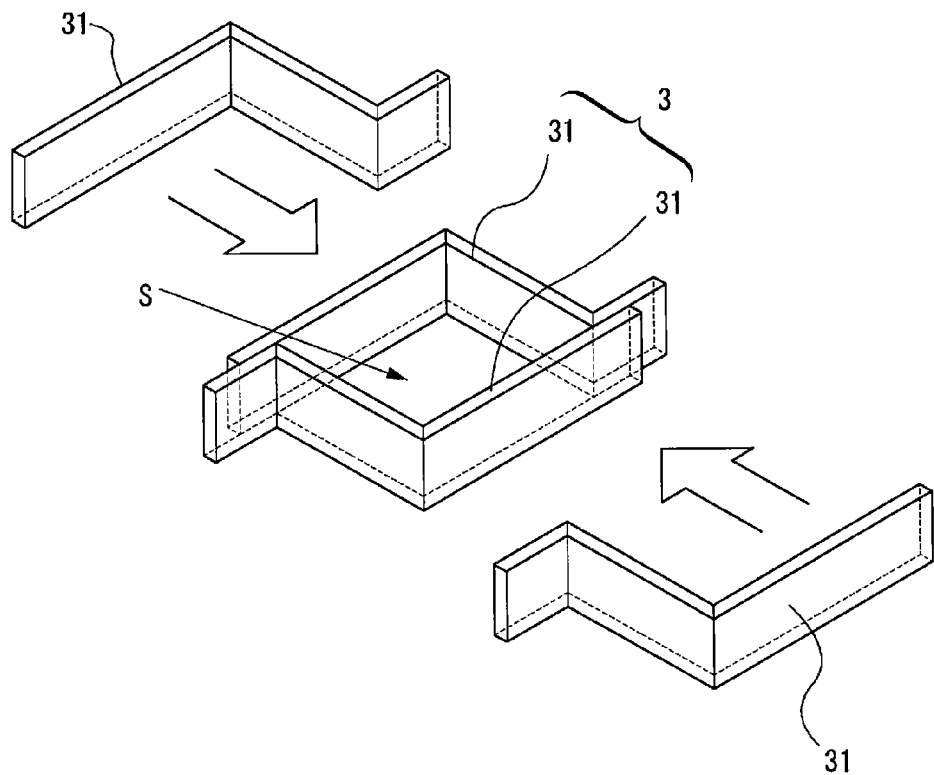
FIG. 5 is an explanatory oblique view of a frame constituting element of the texture embedment preparing portion in an imaginary line.

FIG. 4 is an explanatory oblique view of a texture embedment preparing portion placed on the cutting guide device sown in FIG. 1, illustrating a frame constituting element of the texture embedment preparing portion shown in FIG. 5 in an imaginary line, a dashed-dotted line.

FIG. 5 is an explanatory oblique view of a frame constituting element of the texture embedment preparing portion shown in FIG. 4 in an imaginary line.

The texture section preparing device comprising the cutting guide device 1 shown in FIG. 1 and a texture embedment preparing portion 4 shown in FIG. 4.

Each structural member of the texture section preparing device will be explained further in due order.

First, the cutting guide device 1 will be explained according to FIG. 1 to FIG. 3 hereinafter.

The cutting guide device is used for slicing the texture mass A to obtain the texture slices $A1 \ldots A_N$ from the texture mass A (see also, later described below in the discussion of FIG. 10 and FIG. 11.)

As shown in FIG. 1, the cutting guide device comprises a placing base 11, a cutting guide cover 12, and pressing member 14.

A texture mass A is placed directly or indirectly on the placing base 11. As shown in later described FIG. 9, the cutting guide cover 12 prevents the texture mass A from moving by pressing the texture mass A downward, which is placed on the placing base 11 directly or indirectly.

The top side of the cutting guide cover 12 rotates around the fulcrum shaft 121, 121 which is provided at the base portion side. A pressing member 14 comprises a slippage preventing member which prevents the position of the cutting guide cover 12, which presses the texture mass A, slipped off.

Because the entire cutting guide device 1 is formed of stainless-steel, it is solid, rust resistant, easily washable after use, and always kept under clean condition.

The placing base 11 is in the form of a plate with thickness of 30 mm and has a shape of quadrate or rectangular in planar view. The placing base 11 of the present embodiment has lateral width of 200 mm and longitudinal length of 230 mm. This dimension is not limited to but can be set accordingly depending on the dimensions of the texture mass A, the cutting target.

The surface of the placing base 11 is provided with a flat and smooth placing surface 111. This placing surface 111 is used by setting a texture embedment preparing portion 4 shown in FIG. 4 (see later, described in the discussion of FIG. 6.)

Figure 6:
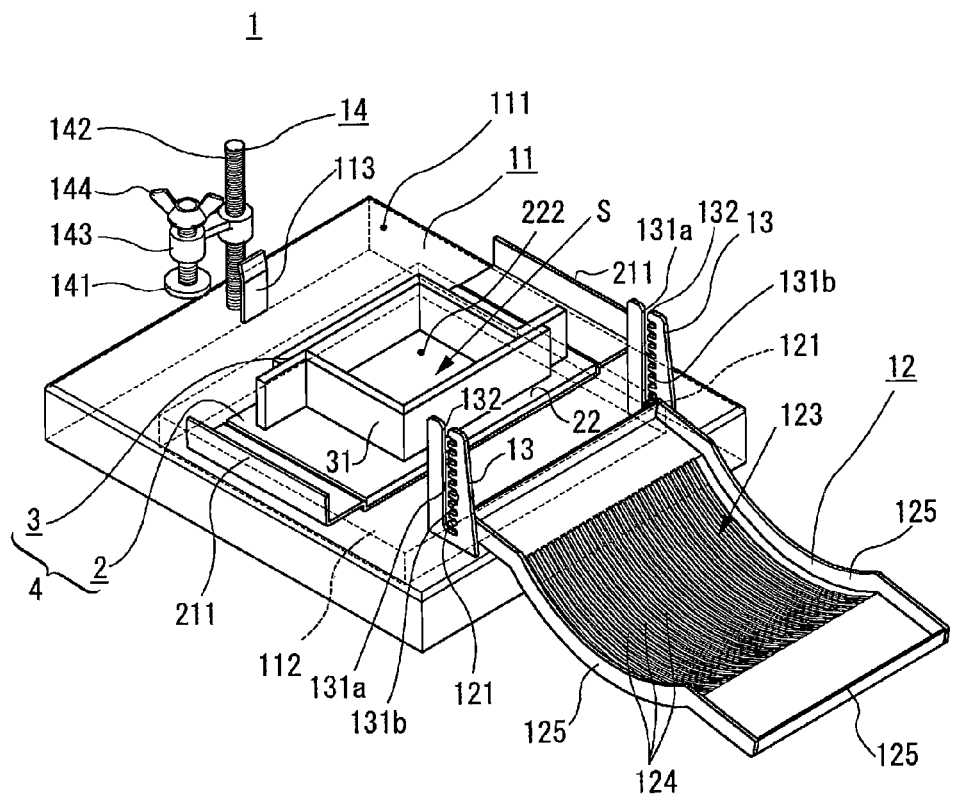
FIG. 6 is an explanatory oblique view illustrating a step of procedures for pressing a texture mass by a cutting guide cover of a cutting guide device.

Further, as shown in FIG. 1 and FIG. 6, a magnet 112 is built inside of the placing base 11. This magnet 112 generates an attractive force between the placing base 11 and a texture mass placing portion 2 made of stainless steel, which is set on the placing surface 111 of the placing base 11. By this attractive force of the magnet 112, the texture mass placing portion 2 is prevented from easily slipping off the placing surface 111.

Further, the attractive force of the magnet 112 is in a degree that the texture mass placing portion 2 is movable, removable and replaceable on the placing base 11. Therefore, when a force resistant to the attractive force of the magnet 112 is applied to the texture mass placing portion 2 to move, the position of the cutting guide cover 12 which presses the texture mass can be adjusted properly after the texture mass placing portion is placed on the placing base 11. Accordingly, the operation is performed at the most proper position.

As shown in FIG. 2, the cutting guide cover 12 is formed in the shape of a rectangular in a planar view. For example, the cutting guide cover 12 is formed by curving the center region of a thin plate of stainless steel to make the curved portion, and further formed entirely, by providing a plurality of slits 124 at the curved portion.

More specifically, a contacting portion 123 which curves or protrudes in an opposite direction to the pressing, in a way to protrude upward when the cutting guide cover 12 is closed, is provided at the position at which at least the texture mass A is pressed.

As shown in FIG. 3, the contacting portion 123 has a rounded surface which is curved or protrudes in upside-down U shape in a side view. The contacting portion 123 is located at the almost center and formed continuously in entire lateral direction of the cutting guide cover 12.

In this embodiment, the dimension of the contacting portion 123 is 120 mm in length and width and maximum curved depth is 30 mm. The dimensions are not limited to but can be determined accordingly in view of the size of the target texture mass.

As shown in later described FIG. 10, during an actual operation, when the texture mass A is held so as to be sandwiched between the closed cutting guide cover 12 and the placing base 11, the contacting portion 123 contact the texture mass A from above.

The contacting portion 123 shown in FIG. 2 is formed with a plurality of slits 124 in which a pathological knife C used for cutting the texture mass A can be inserted. The width of the interval of the plurality of slits 124 is set corresponding to the thickness of the desired texture slices $A_1 \ldots A_N$. In this embodiment, the size of the interval is provided beforehand so as to be able to prepare slices with 3 mm thickness.

Further, the cutting guide cover 12 comprises, at the periphery thereof, a peripheral wall portion 125 in a L like shape in the cross section which is formed in a direction to pressing the texture mass A.

As shown in FIG. 1 and FIG. 2, the turnable cutting guide cover 12 is provided through bearing strips 13, 13 formed at a front side of the placing base 11 (at the right side in FIG. 1), which is a pair of bearing portion set up with required distance. Further, the cutting guide cover 12 can be removed from the bearing strips 13, 13 to separate from the placing base 11. This operation will be described later.

As shown in FIG. 3, each strip of the pair of the bearing strip 13 is formed in a shape of a thin plate. Further, an outer side in a side view, which is right side in FIG. 3, of each bearing strip 13 is formed diagonally in a mountain-like shape, the lateral width of which becomes smaller toward the top end portion.

Each bearing strip 13 supports each of the fulcrum shaft 121, 121 of the cutting guide cover 12 so that the fulcrum shaft 121, 121 can turn and be removable and replaceable. Further, each bearing strip 13 is provided with a first opening portion 131a which guides the fulcrum shaft 121 to move in a vertical direction of the fulcrum shaft 121 for adjusting in a stepwise manner the height of the fulcrum shaft 121. The first opening portion 131a comprises an long opening which is formed in a direction from the lower to the upper of each bearing strip 13. An opening 132 of the first opening portion 131a is formed at the tip of the bearing strip 13.

Further, each bearing strip 13 includes a second opening portion 131b of which required number of openings are formed connecting to the first opening portion 131a from the lower to the upper in a stepwise manner. The second opening portions 131b are formed in the plural required number, which is 10 in this embodiment, and with required intervals in a direction from the lower to the upper of the first opening portion 131a. The second opening portions 131b are formed horizontally, that is to say, in a vertical direction to the first opening 131a. In this embodiment, the second openings 131b are formed as a plurality of short openings in a vertical direction to the first opening portion 131a, more specifically, in the right in FIG. 3, which is at the front of the placing base 11.

Each fulcrum shaft 121 of the cutting guide cover 12 is formed so as to protrude to outside of base end portion of each peripheral wall portions 125 at the both side of the fulcrum shafts 121 in vertical direction. As shown in FIG. 3, usually, by putting each fulcrum shaft 121 to one of the second opening portion 131b of bearing strip 13, 13, the cutting guide cover 12 can be turnable at the placing base 11 at the height corresponding to the second opening portion 131b.

Height adjustment of the cutting guide cover 12 is performed as follows. The tip of the cutting guide cover 12 at its level, which is drawn in a solid line in FIG. 3, is lifted at an angle or slide toward the tip so that each fulcrum shaft 121 moves from the second opening portion 131b to the first opening portion 131a. Then, each fulcrum shaft 121 is moved vertically along the first opening portion 131a to set in another second opening portion 131b at a different height for adjusting the height of the cutting guide cover 12 which is supported on the shaft.

The cutting guide cover 12 can be separated from the placing base 11 by removing the fulcrum shaft 121 from the opening 132 at the tip of each bearing strip 13. By this, the cutting guide cover 12 shown in FIG. 2 can be replaced with a cutting guide cover in a various mode.

When a cutting guide cover having a various slit interval is used in place of the cutting guide cover 12 shown in FIG. 2, slices in various thickness can be prepared properly. That is to say, by replacing only the component, the cutting guide cover 12, not the cutting guide device itself, sections in desired thickness can be prepared properly.

Further, depending on the dimension or shape of the cutting target texture mass A, another cutting guide cover having a contacting portion 123 of various curvature can be used.

Further, the cutting guide cover 12 which contact the texture mass A can be washed thoroughly by removing from the placing base 11 after use. Thus, even when the placing base 11 has a substantial weight, the removed cutting guide cover is light enough to be washed.

As shown in FIG. 1 and FIG. 2, a pressing member 14 is formed near the center of the tip side of the placing surface 111 of the placing base 11. As described above, the pressing member 14 prevents the cutting guide cover 12 from moving off the position to press the texture mass A.

The pressing member 14 includes a bracing strut portion 142, a supporting portion in a shape of stick which is formed vertically on the placing surface 111; connecting portion 143 which extends to the side from the bracing strut portion 142; the pressing part 141 which is formed downward from the tip of the connecting portion 143.

In this embodiment, the bracing strut portion 142 comprises bolt shaft having a screw thread. The base tip portion of the connecting portion 143 has a screw hole for the bracing strut portion 142. The height and direction of the connecting portion 143 can be adjusted by rotating the connecting portion 143 horizontally.

A bolt hole is formed at the tip portion of the connecting portion 143. This bolt hole is formed for wing screw 144 which is a height adjusting portion in a stick shape having the pressing part at the lower thereof. By rotating the wing screw 144 manually to move the wing screw up and down, the height of the pressing part 141 can be adjusted flexibly. Further, when the height is adjusted, the pressing part 141 presses the tip-side surface 127 of the cutting guide cover 12.

As shown in FIG. 3, near the bracing strut portion 142, a retainer strip 113 is formed for preventing the cutting guide cover from moving toward the end side by retaining peripheral wall portion 125 at the end side of the cutting guide cover 12 when it is closed.

As shown in FIG. 2, on the surface 126 at the front of the cutting guide cover 12 (at the right side in FIG. 2, closer to bearing strip 13, 13), a scale is marked for measuring the number of the cut sections corresponding to the position of the plurality of slits 124.

Texture embedment preparing portion 4 will be explained referring to FIG. 4 and FIG. 5.

Texture embedment preparing portion 4 has a texture placing portion 2 that has a placing surface 222 for placing the texture mass A and a frame constituting element 3 that includes a housing portion S for placing the texture mass A and an embedding agent B by acting together with the placing surface 222 in a combination with the texture placing portion 2.

As shown in later described FIG. 6, the texture placing portion 2 shown in FIG. 4 is used by being put on the placing surface 111 of the cutting guide device 1. The texture placing portion 2 has a relatively long rectangular shape in a planar view and comprises main frame body 21 made from a stainless steel and the placing part 22 made from a synthetic resin in a thin plate shape.

Both sides of the main frame body 21 comprise grippers 211, 211 in L shape. The placing part 22 which is made from a synthetic resin is fixed with adhesive and others so as not to be removed by fitting into the hollow portion 212 at the center of the main frame body 21. The placing part 22 is formed from a synthetic resin with a lasting grip to prevent the texture mass A placed on the placing surface 222 from slipping off.

Because the placing part 22 is used for placing fresh body texture, it is preferred to be kept clean after use. The placing part 22 is preferably formed with a synthetic resin in white or pale color so that an operator can secure body fluid, such as blood, is washed off.

Further, by using the texture placing portion 2, the texture mass A is placed on the texture placing portion 2 and set indirectly on the cutting guide device 1, not placed directly on the placing surface 111 of the cutting guide device 1. Therefore, an operator has only to ensure a thorough washing for the texture placing portion 2 which contacts the texture mass A, but not for the placing surface 111 of the cutting guide device 1. Even when the placing base 11 of the cutting guide device 1 has a substantial weight, washing is easily performed without washing the placing base 11 thoroughly.

The frame constituting element 3 shown in FIG. 4 and FIG. 5 includes a pair of frame member 31, 31 made from stainless steel. Each of the frame member 31, 31 is bent twice at right angle and is formed generally in a hook-shape in a planar view.

When in use, as shown in FIG. 4 and FIG. 5, the frame member 31, 31 are combined by being arranged face to face on the texture placing portion 2. By this, a rectangular housing portion S, which is used for accommodating the texture mass A and a embedding agent B is formed between the frame member 31, 31. (See FIG. 7 described later.)

By sliding the frame member 31, 31 to alter the combined position, the area of housing portion S can be adjusted. By this, a texture mass A in various size can be used.

Drawings from FIG. 6 to FIG. 11 are oblique views explaining a preparing method for a texture section by using the aforementioned texture section preparing device.

Drawings from FIG. 6 to FIG. 9 are oblique views explaining the procedures leading to the operation in which the texture mass is pressed by a cutting guide cover of the cutting guide device.

Figure 10:
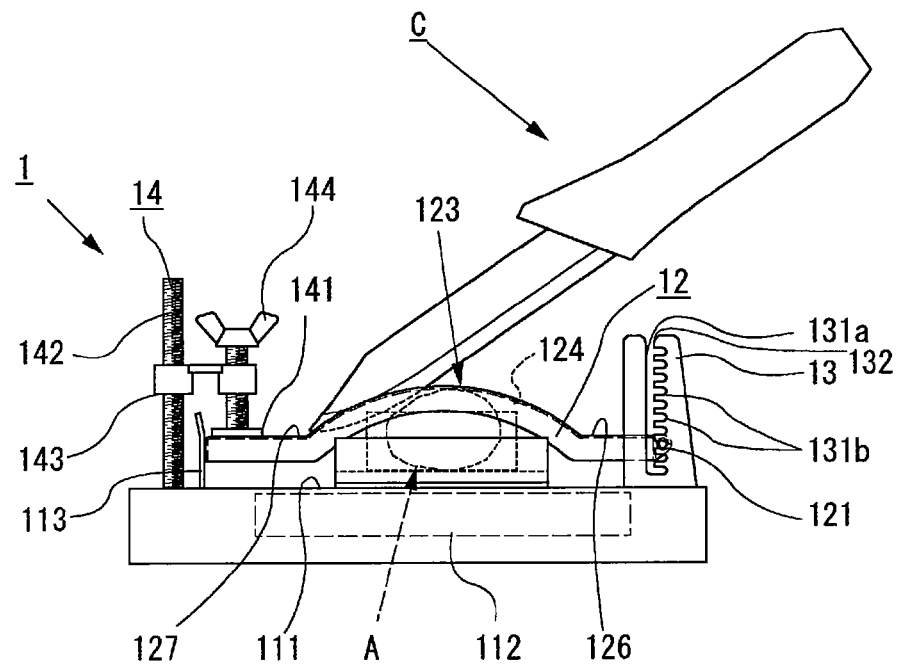
FIG. 10 is a explanatory side view illustrating a condition in which the fixed texture mass is being cut by a pathological knife.
Figure 11:
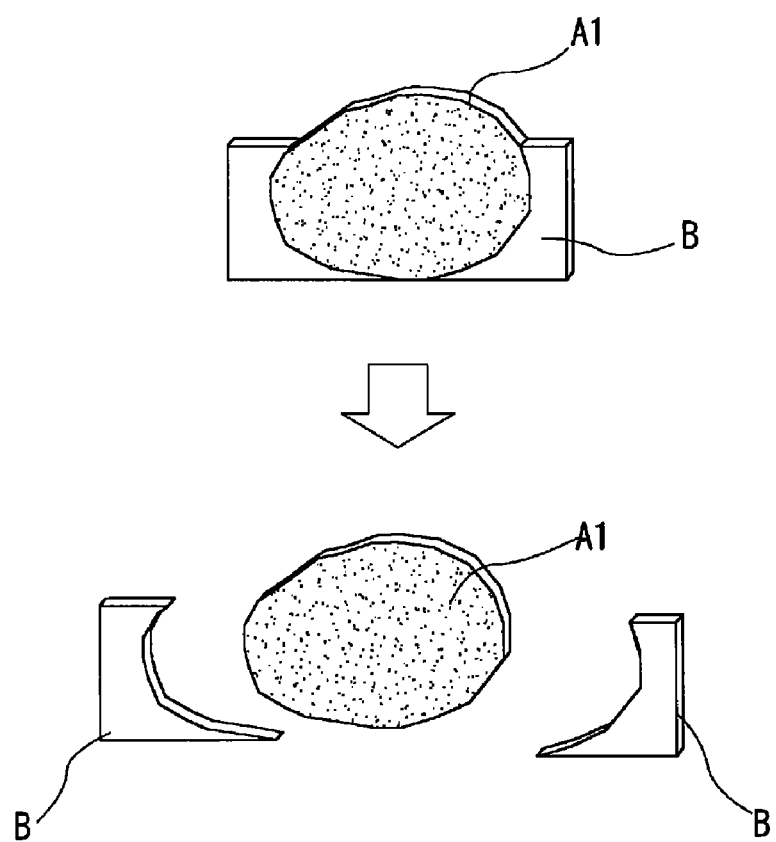
FIG. 11 is an explanatory view illustrating a condition of a section after being removed.

FIG. 10 is an explanatory side view illustrating a condition when a texture mass is being cut by a pathological knife, and FIG. 11 is an explanatory view illustrating a condition of the texture slice after cut.

In FIG. 11, the thickness of the texture slice A1 after cut is relatively overdrawn.

The method for preparing the texture each slices A1 respectively, will be explained hereinafter by referring to from FIG. 6 to FIG. 11.

First, as shown in FIG. 6, the cutting guide cover of the cutting guide device is opened to place the texture placing portion 2 of the texture embedment preparing portion 4 on the placing surface 111 thereof. Next, after a pair of the frame member 31, 31 comprises the texture embedment preparing portion 4 is placed on the texture placing portion 2, the alignment of the combined frame member 31, 31 is adjusted to form the housing portion S in proper size for housing the texture mass A.

Figure 7:
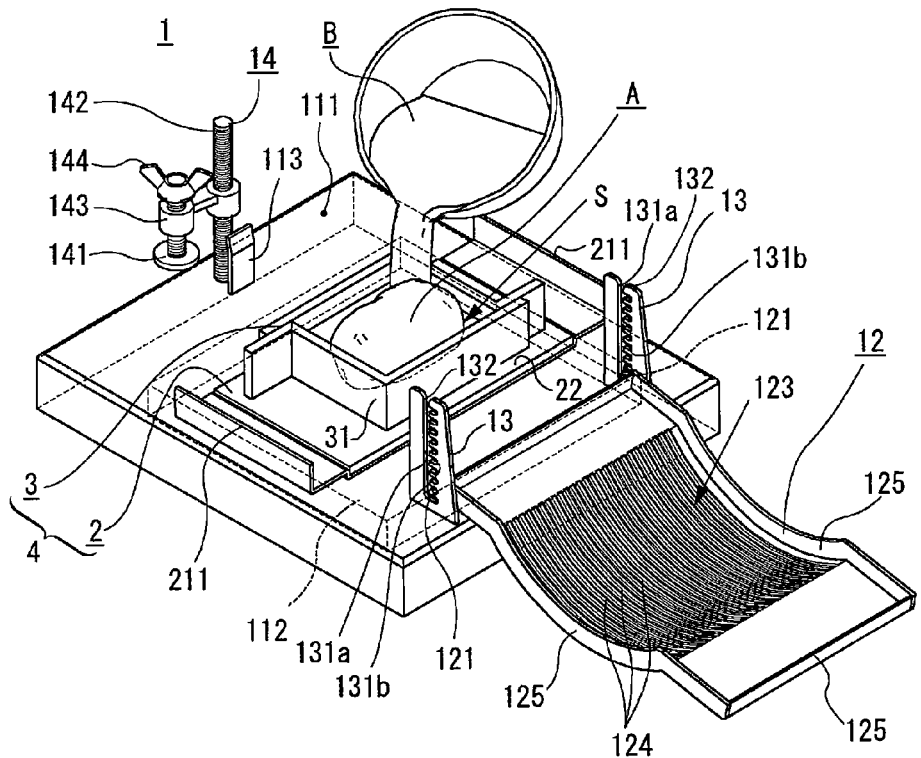
FIG. 7 is an explanatory oblique view illustrating a step of the procedures for pressing a texture mass by a cutting guide cover of a cutting guide device.

As shown in FIG. 7, after the texture mass A is set and placed in the housing portion S, the embedding agent B is poured into at least one of the surface of or a lower side of the housing portion S. This operation can be performed before the texture placing portion 2 is placed to the cutting guide device 1.

In this embodiment, alginate impression material which is usually used as a material for molding teeth and others in dental treatments is used. Alginate impression material is a synthetic resin of which main component is aliginic acid salt and has a triturate type which becomes a paste by mixed with water and a paste type which is preprocessed in a paste with water. Both types can be used.

Figure 8:
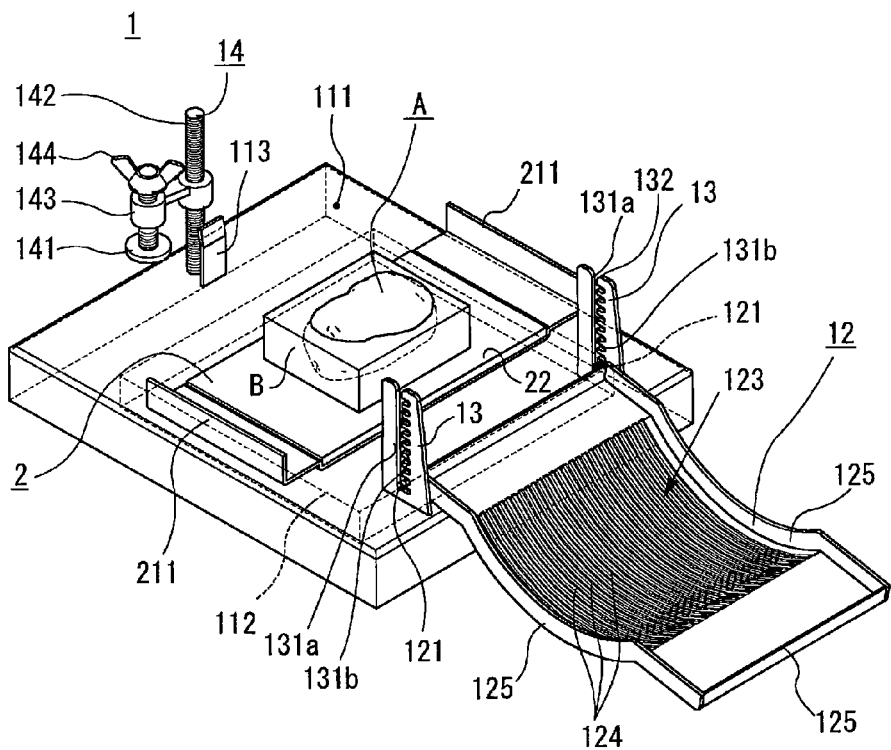
FIG. 8 is an explanatory oblique view illustrating a step of the procedures for pressing a texture mass by a cutting guide cover of a cutting guide device.

After the embedding agent B becomes solidified, as shown in FIG. 8, the frame constituting element 3 (frame member 31, 31) is removed. Subsequently, the texture mass A is adjusted at the best position to the cutting guide cover 12 in a manner in which the gripper 211 is gripped for sliding the texture placing portion 2.

As described above, the texture placing portion 2 of the texture embedment preparing portion 4 functions as a part (the bottom) of the embedding container during the embedding, and as a placing part for placing the texture mass A when the texture mass A is set on the cutting guide device 1.

Therefore, when the texture embedment preparing portion 4 of the present embodiment is used, the embedded texture mass A can be set on the cutting guide device 1 without being touched by operator's hand. Accordingly, the properly embedded texture mass A is prevented from collapse and deformation caused by hand touching.

Further, contrary to the case in which the texture mass A is placed directly on the cutting guide device 1, the texture placing portion 2 can be washed thoroughly after use. Therefore, even when the cutting guide device has a substantial weight, washing process is performed easily.

Figure 9:
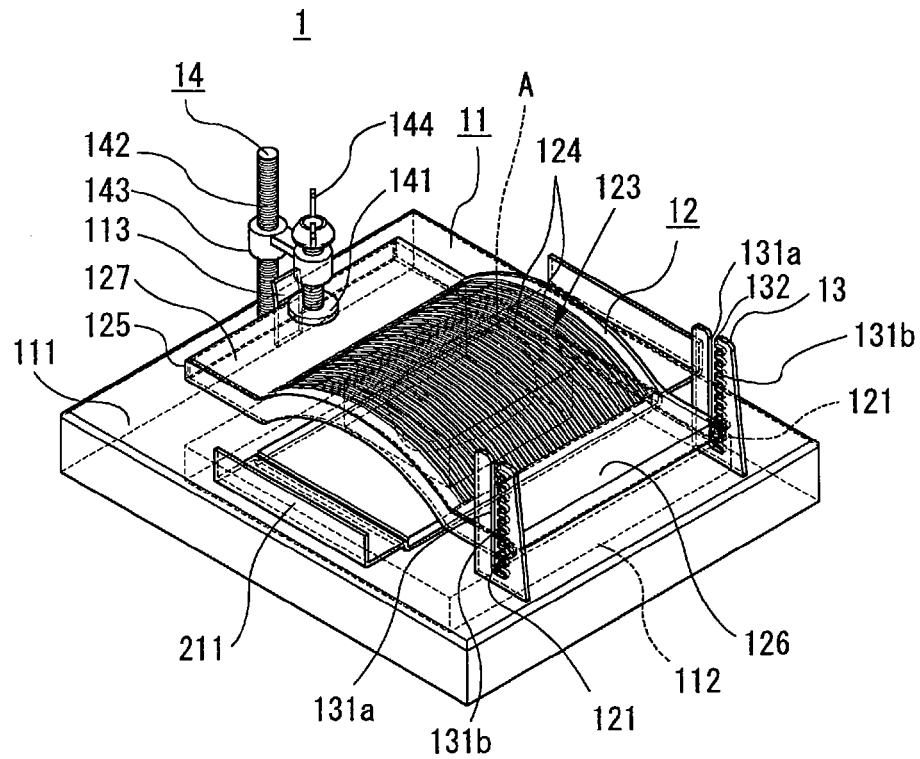
FIG. 9 is an explanatory oblique view illustrating a step of the procedures for pressing a texture mass by a cutting guide cover of a cutting guide device.

As shown in FIG. 9, the texture mass A is pressed downward with the curved contacting portion 123 while the cutting guide cover 12 is closed. Then, after the direction of the connecting portion 143 of the pressing member 14 is moved toward the cutting guide cover 12, the screw bolt 144 is rotated manually to lower the pressing portion 141 for pressing the upper surface 127 of the cutting guide cover 12. By this, the pressing position of the cutting guide cover 12 is prevented from slipped off.

Then, as shown in FIG. 10, the texture mass A is cut into sections one by one by inserting a pathological knife along the plurality of slits 124 and the desired each texture slices A1 are obtained. Preferably, the cutting operation is performed by inserting a pathological knife C, at an angle, into the plurality of each slits 124 from the tip side to applying force gradually toward the bottom. As shown in FIG. 11, after the texture mass A is sliced together with solidified embedding agent B, the resulting each texture slices are removed from the embedding agent B.

As described above, in the present embodiment, after at least one of the surface of or a lower side of the texture mass A is embedded with alginate impression material to be fixed, the texture mass A is pressed downward by the cutting guide cover 12 of the cutting guide device 1. In this manner, embedding the texture mass A by the embedding agent B allows the texture mass A to be less deformable during the cutting, further, less slippery on the placing base 11.

Because alginate impression material is solidified from a fluid state or a paste state, in a very short time, the operation is performed efficiently during the texture embedding/fixing. Further, because the embedding agent is easy to remove from the obtained texture slices, the thin sliced texture slices are less damaged.

As described above, the texture mass A of the parenchymal organs and others is soft with high flexibility and elasticity. Therefore, by pressing downward with the cutting guide cover 12 formed with a plurality of slits 124, the part of the upper side of the texture mass A is dug into the slits one by one. By this, the texture mass A is prevented from being deformed or moved, when it is under a load by a knife (C) when cutting, accordingly, the obtained texture sections are prevented from forming irregular cross-section surfaces.

The width of the intervals of the plurality of slits 124 formed at the cutting guide cover 12 is set corresponding to the thickness of the desired texture slice A1. Thus, when a pathological knife C is inserted along with the one of the plurality of slits 124 to cut the texture mass A, the texture section with uniform thickness can be prepared without experience and skill.

Further, because the texture mass A is prevented from moving by being held between the placing base 11 and the cutting guide cover 12, a texture mass in various width can be used flexibly. The cutting guide cover 12 includes a curved or protruded contacting portion 123 provided in the opposite direction of the pressing. Generally, a texture mass of thick parenchymal organs, for example, prostate gland, lacteal gland, lung, liver, heart, has a rounded outer shape. Thus, by forming the contacting portion 123 curved or protruded to fit the roundness, the entire tissue mass A is pressed by uniform suppression strength as far as possible to prevent from deformation of the texture mass A. By this, the texture slice A1 is securely prevented from irregular cross-sections and has smooth surfaces.

As shown in FIG. 3, the height of the cutting guide cover 12 is adjustable in a stepwise manner. Thus, the texture mass A in a various thickness can be used flexibly. Furthermore, because the height of the fulcrum shaft 121 of the cutting guide cover 12 is adjustable, the texture mass A can be pressed allowing the cutting guide cover horizontal or as far as horizontal.

By this, for example, comparing to pressing the texture mass A downward at slant by the cutting guide cover 12, the suppression strength is prevented to be applied excessively to a part of the texture mass A and, accordingly, deformation of the texture mass A is prevented. By this, irregularity of the obtained texture section A1 can be more securely prevented.

The terms and expressions used in the present specification are used only for a explanatory purpose and are not to be considered to be limited. Terms and expressions similar to those used above are not excluded. Further, the present invention is not to be considered to be limited to the embodiment shown in the drawings, and can devised with a scope of known technical ideas.

In the scope of claims, codes used in drawings are noted with parenthesis in order to help understandings of claim descriptions, however, the scope of claims is not to be considered to be limited to those illustrated in the drawings.

According to the cutting guide device for preparing texture slices, the texture slices preparing device and method of preparing texture slices relating to the present invention, a texture slices can be prepared manually with a cutting tool such as a pathological knife, in a uniform thickness and in a regular section with neither experience not skill. Further, a texture mass in a various thickness can be used flexibly.

According to the cutting guide device for preparing texture slices in which the cutting guide cover is removable and replaceable. Because the cutting guide cover can be removed from the cutting guide device, washing of the cutting guide cover can be performed easily. Further, it is very convenient that the cutting guide cover can be replaced accordingly to those in different modes, which have different intervals of the plurality of slits for preparing the different thickness of the texture slices or fit to the texture mass in different shapes.

According to the cutting guide device having a texture embedment preparing portion, the texture mass can be set on the cutting guide device without touched by hand after embedded. Accordingly, when embedded properly, the texture mass is prevented from corruption or deformation caused by hand touching. Further, contrary to a case in which the texture mass is placed directly on the cutting guide device, the texture placing portion can be washed thoroughly after use. Thus, even when the cutting guide device has a substantial weight, washing is easily performed.

When the cutting guide device includes the texture embedment preparing portion which can adjust the area of the housing portion for accommodating the texture mass and embedding agent, the appropriate amount of the embedding agent is used.

When a cutting guide device has a magnet formed between the placing base and the texture mass placing portion, the feature can prevent inconveniences, for example, in which the texture mass pressed by the cutting guide cover slips out of the place by the slippage of the texture placing portion. Further, even after the texture mass is placed on the texture placing portion, the position of the texture mass corresponding to the cutting guide cover can be adjusted properly to allow the cutting operation is performed at the best position.

By using a dental impression agent as an embedding agent, a texture mass in various size and shape can be embedded properly, cutting operation can be performed by a blade such as a pathological knife and others, and texture slices can be obtained without irregular slices. Further, because alginate impression material or silicone rubber impression material become solidified from fluid state form or paste form, in a very short time, texture embedding operation is performed efficiently.

Furthermore, alginate impression material is preferable, because alginate impression material can be removed much easily from the obtained texture slices after cut and prevents damage of a thin texture section.

The invention claimed is:

1. A cutting guide device for slicing a texture mass to obtain texture slices, comprising:
a placing base for placing the texture mass directly or indirectly thereon;
a cutting guide cover preventing said texture mass placed directly or indirectly on said placing base from moving by holding the texture mass downward in a manner in which an end potion side rotates around fulcrum shafts provided on a base side portion; and
a pressing member preventing the cutting guide cover from being displaced with respect to the texture mass held by the cutting guide cover;
wherein
a contacting portion is so formed to curve or protrude in an opposite direction to the pressing direction at least in a portion of the cutting guide cover which presses the texture mass;
a plurality of slits, into which a knife to be used for cutting the texture mass can be inserted, are formed at said contacting portion;
the plurality of slits are provided with intervals therebetween which are set to a thickness of each desired texture slices;
the placing base has bearing portions which support and enable the fulcrum shafts to rotate and to be removable and replaceable;
the bearing portions have at least one of opening portions, pores, or insections, which guide the fulcrum shafts to be moved in a vertical direction with respect to the fulcrum shafts for adjusting the height of the fulcrum shafts; and
the pressing member comprises:
a bracing strut portion having a screw thread and formed vertically on a placing surface of the placing base;
a connecting portion which extends to the side from the bracing strut portion; and
a pressing part which is formed downward from a tip of the connecting portion;
wherein
a base tip portion of the connecting portion has a screw hole for the bracing strut portion, and the height and direction of the connecting portion can be adjusted by rotating the connecting portion horizontally; and
a bolt hole is formed at a tip portion of the connecting portion, said bolt hole is formed for a screw which is provided with the pressing part at a lower end thereof, and by rotating the screw to move the screw up and down, the height of the pressing part can be adjusted so that the pressing part presses a tip-side surface of the cutting guide cover.

2. A texture slices preparing device for preparing texture slices by slicing a texture mass, comprising;
a cutting guide device as set forth in claim 1, and
a texture embedment preparing portion for preparing an embedded texture mass, wherein
the texture embedment preparing portion comprises:
a texture placing portion having a placing surface for the texture mass, and
a frame constituting element which, in combination with the texture placing portion, acts together with said placing surface to form a housing portion accommodating the texture mass and an embedding agent.

3. The texture slices preparing device as set forth in claim 2, wherein the frame constituting element comprises:
a frame member which, in combination with the texture placing portion, acts together with said placing surface to adjust the area of the housing portion.

4. The texture slices preparing device as set forth in claim 2, wherein the frame constituting element comprises:
a pair of frame members arranged face to face on said texture placing portion to adjust the area of the housing portion by changing the positions of the frame members.

5. The texture slices preparing device as set forth in claim 2, further comprising:
a magnet provided on at least one of a placing base of the cutting guide device and the texture placing portion of the texture embedment preparing portion generating an attractive force between the placing base and texture placing portion, the attractive force allowing the texture placing portion to be movable or removable with respect to the placing base.

6. The texture slices preparing device as set forth in claim 3, further comprising:
a magnet provided on at least one of the placing base of the cutting guide device and the texture placing portion of the texture embedment preparing portion generating an attractive force between the placing base and texture placing portion, the attractive force allowing the texture placing portion to be movable or removable with respect to the placing base.

7. The texture slices preparing device as set forth in claim 4, further comprising:
a magnet provided on at least one of a placing base of the cutting guide device and the texture placing portion of the texture embedment preparing portion generating an attractive force between the placing base and texture placing portion, the attractive force allowing the texture placing portion to be movable or removable with respect to the placing base.

8. The cutting guide device as set forth in claim 1, wherein a retainer strip is formed near the bracing strut portion for preventing the cutting guide cover from moving toward an end side by retaining a peripheral wall portion at the end side of the cutting guide cover when it is closed.

9. The cutting guide device as set forth in claim 1, wherein a scale is marked on a surface at the front of the cutting guide cover for measuring the number of cut sections corresponding to the position of the plurality of slits.

10. The cutting guide device as set forth in claim 1, wherein a part of the upper side of the texture mass is dug into the plurality of slits by pressing downward with the cutting guide cover, thereby preventing the texture mass from being deformed or moved.

11. The cutting guide device as set forth in claim 1, wherein the screw provided with the pressing part is a wing screw.

12. A texture slices preparing device for preparing texture slices by slicing a texture mass, comprising;
   a cutting guide device as set forth in claim 11, and
   a texture embedment preparing portion for preparing an embedded texture mass, wherein
   the texture embedment preparing portion comprises:
      a texture placing portion having a placing surface for the texture mass, and
      a frame constituting element which, in combination with the texture placing portion, acts together with said placing surface to form a housing portion accommodating the texture mass and an embedding agent.

13. The texture slices preparing device as set forth in claim 12, wherein the frame constituting element comprises:
   a frame member which, in combination with the texture placing portion, acts together with said placing surface to adjust the area of the housing portion.

14. The texture slices preparing device as set forth in claim 13, further comprising:
   a magnet provided on at least one of the placing base of the cutting guide device and the texture placing portion of the texture embedment preparing portion generating an attractive force between the placing base and texture placing portion, the attractive force allowing the texture placing portion to be movable or removable with respect to the placing base.

15. The texture slices preparing device as set forth in claim 12, wherein the frame constituting element comprises:
   a pair of frame members arranged face to face on said texture placing portion to adjust the area of the housing portion by changing the positions of the frame members.

16. The texture slices preparing device as set forth in claim 15, further comprising:
   a magnet provided on at least one of the placing base of the cutting guide device and the texture placing portion of the texture embedment preparing portion generating an attractive force between the placing base and texture placing portion, the attractive force allowing the texture placing portion to be movable or removable with respect to the placing base.

17. The texture slices preparing device as set forth in claim 12, further comprising:
   a magnet provided on at least one of a placing base of the cutting guide device and the texture placing portion of the texture embedment preparing portion generating an attractive force between the placing base and texture placing portion, the attractive force allowing the texture placing portion to be movable or removable with respect to the placing base.

18. The cutting guide device as set forth in claim 11, wherein a retainer strip is formed near the bracing strut portion for preventing the cutting guide cover from moving toward an end side by retaining a peripheral wall portion at the end side of the cutting guide cover when it is closed.

19. The cutting guide device as set forth in claim 11, wherein a scale is marked on a surface at the front of the cutting cover for measuring the number of cut sections corresponding to the position of the plurality of slits.

20. The cutting guide device as set forth in claim 11, wherein a part of the upper side of the texture mass is dug into the plurality of slits by pressing downward with the cutting guide cover, thereby preventing the texture mass from being deformed or moved.

* * * * *